US006417146B1

(12) United States Patent
Miyajima et al.

(10) Patent No.: US 6,417,146 B1
(45) Date of Patent: Jul. 9, 2002

(54) AQUEOUS LIQUID DETERGENT COMPOSITIONS HAVING A SURFACTANT, FATTY ACID GLYCOL ESTER AND A GLYCERYL ETHER

(75) Inventors: Tetsuya Miyajima, Wakayama; Kennichi Kasuga, Tokyo, both of (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/685,083

(22) Filed: Oct. 11, 2000

(30) Foreign Application Priority Data

Nov. 12, 1999 (JP) .......................................... 10-289877

(51) Int. Cl.[7] ............................................... A61K 31/08

(52) U.S. Cl. ....................... 510/130; 510/136; 510/156; 510/505; 510/506; 424/70.1; 514/723

(58) Field of Search ................................ 510/130, 136, 510/156, 505, 506; 424/70.1; 514/723

(56) References Cited

U.S. PATENT DOCUMENTS

| | | | |
|---|---|---|---|
| 2,091,162 | A | 8/1937 | Schrauth |
| 2,157,022 | A | 5/1939 | Schrauth |
| 2,900,346 | A | 8/1959 | Fowkes et al. |
| 4,178,382 | A | 12/1979 | Mao et al. |
| 4,430,237 | A | 2/1984 | Pierce et al. |
| 6,040,347 | A | 3/2000 | Cupferman et al. |

FOREIGN PATENT DOCUMENTS

| | | |
|---|---|---|
| DE | 4 140 474 | 6/1993 |
| DE | 19 500 688 | 7/1996 |
| DE | 195 08 857 | 9/1996 |
| EP | 0 422 862 | 4/1991 |
| EP | 0 485 212 | 5/1992 |
| EP | 0 487 262 | 5/1992 |
| GB | 1 560 083 | 1/1980 |
| WO | WO 95/14073 | 5/1995 |
| WO | WO 98/22081 | 5/1998 |

*Primary Examiner*—Necholus Ogden
(74) *Attorney, Agent, or Firm*—Oblon, Spivak, McClelland, Maier & Neustadt, P.C.

(57) ABSTRACT

An aqueous liquid detergent composition comprises:

(A) 1 to 50 wt. % of a surfactant selected from an anionic surfactant, a nonionic surfactant or an amphoteric surfactant;

(B) 0.3 to 5 wt. % of a long-chain fatty acid glycol ester represented by the following formula (1):

(1)

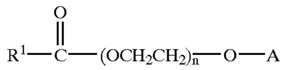

wherein $R^1$ represents a linear or branched, $C_{13-23}$ alkyl or alkenyl group, n stands for an integer of 1 to 3, and A represents H or 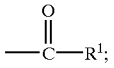

and (C) 0.1 to 10 wt.% of a glyceryl ether having one or more linear or branched, $C_{4-12}$ alkyl or alkenyl groups.

14 Claims, No Drawings

AQUEOUS LIQUID DETERGENT COMPOSITIONS HAVING A SURFACTANT, FATTY ACID GLYCOL ESTER AND A GLYCERYL ETHER

BACKGROUND OF THE INVENTION a) Field of the invention

This invention relates to detergent compositions, each of which has a pearly luster and is excellent in the dispersion stability of a pearlant.

b) Description of the Related Art

In detergents such as shampoos, face washes and body washes, it has been the conventional practice to alter their appearances to have a pearly luster so that they can be provided with an additional commercial value.

Nowadays, a detergent composition with a pearly luster is primarily obtained by using a long-chain fatty acid glycol ester, which is in a solid form at room temperature, or the like as a pearlant, adding the pearlant at room temperature upon production of a detergent, heating the resulting mixture until the pearlant melts, and then cooling the heated mixture back to have the pearlant crystallized; or by mixing a thick dispersion, which has been obtained beforehand by melting the pearlant and cooling it back and has a pearly luster, with detergent ingredients at room temperature. Whichever method is used, the pearlant is dispersed as fine crystals in the final composition.

However, conventional detergent compositions, which have been obtained as described above and have a pearly luster, are not sufficient in terms of providing stability for the dispersed pearlant and, especially when stored for a long time, may undergo separation and develop precipitation in some instances.

SUMMARY OF THE INVENTION

An object of the present invention is to provide a detergent composition, which is excellent in the dispersion stability of a pearlant and has a long-lasting beautiful pearly luster.

The present inventors have found that use of a specific glyceryl ether along with a particular pearlant makes it possible to obtain a detergent composition, which is excellent in the dispersion stability of the pearlant and, even when stored over a long time, does not undergo separation and develop precipitation and has a long-lasting beautiful pearly luster.

The present invention, therefore, provides an aqueous liquid detergent composition comprising the following ingredients (A), (B) and (C):

(A) 1 to 50 wt. % of a surfactant selected from an anionic surfactant, a nonionic surfactant or an amphoteric surfactant;

(B) 0.3 to 5 wt. % of a long-chain fatty acid glycol ester represented by the following formula (1):

(1)

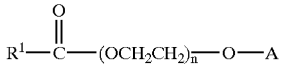

Wherein $R^1$ represents a linear or branched, alkyl or alkenyl group having 13 to 23 carbon atoms, n stands for an integer of 1 to 3, and A represents a hydrogen atom or a group

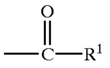

in which $R^1$ has the same meaning as defined above; and (C) 0.1 to 10 wt. % of a glyceryl ether having one or more linear or branched, alkyl or alkenyl groups having 4 to 12 carbon atoms.

The detergent composition according to the present invention contains the pearlant in a stably dispersed form, has a beautiful pearly luster, and moreover, remains stable over a long time. The detergent composition, therefore, gives a sense of richness and a sense of warmth to users.

DETAILED DESCRIPTION OF THE INVENTION AND PREFERRED EMBODIMENTS

The surfactant employed as the ingredient (A) in the present invention is selected from an anionic surfactant, a nonionic surfactant or an amphoteric surfactant.

Preferred examples of the anionic surfactant can include sulfates, sulfonates and carboxylates. Illustrative are alkyl sulfates, polyoxyalkylene alkyl ether sulfates, polyoxyalkylene alkenyl ether sulfates, alkyl sulfosuccinates, alkyl polyoxyalkylenesulfosuccinates, alkylbenzene sulfonates, α-olefinsulfonates, polyoxyalkylene alkyl phenyl ether sulfates, glyceride sulfates, amideether sulfates, higher fatty acid salts, alkanesulfonates, and α-sulfofatty acid ester salts.

Among these anionic surfactants, alkyl sulfates, polyoxyalkylene alkyl ether sulfates and polyoxyalkylene alkenyl ether sulfates are particularly preferred. More preferred are alkyl sulfates represented by the following formula (2) and also, polyoxyalkylene alkyl ether sulfates and polyoxyalkylene alkenyl ether sulfates represented by the following formula (3):

$$R^2OSO_3M \quad (2)$$

$$R^3O(CH_2CH_2O)_mSO_3M \quad (3)$$

wherein $R^2$ represents an alkyl group having 10 to 18 carbon atoms, $R^3$ represents an alkyl or alkenyl group having 10 to 18 carbon atoms, M represents an alkali metal atom, an alkaline earth metal atom, an ammonium ion, an alkanol amine residue or a basic amino acid residue, and m stands for an integer of from 1 to 5 in terms of weight average.

Examples of the nonionic surfactant can include polyoxyalkylenealkyl ethers, polyoxyalkylene fatty acidesters, polyoxyalkylene sorbitan fatty acid esters, polyoxyalkylene sorbitol fatty acid esters, polyoxyalkylene glycerin fatty acid esters, monoglycerides, sorbitan fatty acids, fatty acid alkanolamides (fatty acid monoethanolamides, fatty acid diethanolamides, and the like), and alkyl polyglycosides. Of these, fatty alkanolamides and polyoxyalkylene alkyl ethers are particularly preferred.

Examples of the amphoteric surfactant can include fatty acid amidopropyl betaines, betaine acetates, betaine amidoacetates, sulfobetaines, amidosulfobetaines, phosphobetaines, alkylamine oxides, and amidoamineoxides. Of these, fatty acid amidopropyl betaines are particularly preferred.

As the ingredient (A) in the present invention, it is preferred to combine an anionic surfactant with a nonionic surfactant and/or an amphoteric surfactant. It is more preferred to combine such that an anionic surfactant and a fatty acid amidopropyl betaine, fatty acid alkanolamide or polyoxyalkylene alkyl ether are included.

As the ingredient (A), one or more surfactants can be used. The ingredient (A) amount to 1 to 50 wt. %, preferably 10 to 50 wt. %, notably 10 to 22 wt. of the whole composition. This range is preferred as good cleansing power is available.

As the ingredient (B), i.e., the long-chain glycol ester (1) for use in the present invention, an ester of the formula (1) in which $R^1$ is an alkyl group having 13 to 23 carbon atoms, especially an alkyl group having 18 carbon atoms is preferred. Illustrative are ethylene glycol monostearate, ethylene glycol monopalmitate, ethylene glycol distearate, ethylene glycol dibehenate, diethylene glycol monostearate, diethylene glycol monopalmitate, diethylene glycol distearate, and triethylene glycol monostearate.

Particularly preferred as the ingredient (B) is ethylene glycol distearate.

One or more long-chain fatty acid glycol esters (1) can be used as the ingredient (B). The ingredient (B) amounts to 0.3 to 5 wt. %, preferably 0.5 to 5 wt. %, notably 0.8 to 3 wt. % of the whole composition. This range is preferred because a beautiful pearly luster and good stability are available.

The glyceryl ether as the ingredient (C) contains one or more linear or branched, alkyl or alkenyl groups having 4 to 12 carbon atoms. Preferred examples can include glyceryl ethers containing one or more alkyl groups having 4 to 12 carbon atoms, such as n-butyl, isobutyl, tert-butyl, n-pentyl, isopentyl, n-hexyl, isohexyl, n-heptyl, n-octyl, 2-ethylhexyl, n-nonyl, isononyl, n-decyl and/or n-lauryl groups. Particularly preferred are glyceryl ethers containing one or two alkyl groups, especially one alkyl group having 4 to 11 carbon atoms, more preferably 6 to 11 carbon atoms, notably 8 carbon atoms.

As the ingredient (C), one or more glyceryl ethers can be used. The ingredient (C) amounts to 0.1 to 10 wt. %, preferably 0.5 to 5 wt. %, notably 1 to 5 wt. % of the whole composition. This range is preferred because a beautiful pearly luster and good stability are available.

The detergent composition according to the present invention may further contain a silicone, and the resulting detergent composition can bring about excellent conditioning effect. It has been difficult to have a silicone stably contained in conventional aqueous liquid detergent compositions. In the present invention, however, the inclusion of the glyceryl ether as ingredient (C) has made it possible to stably disperse a silicone.

Examples of the silicone can include:

(1) Dimethylpolysiloxanes represented by the following formula:

$$(Me_3)SiO—(Me_2SiO)_n—Si(Me_3)$$

wherein Me represents a methyl group and n stands for a number of from 3 to 20,000.

(2) Amino-modified silicones:

Although a variety of amino-modified silicones are usable, particularly preferred is the amino-modified silicone described under the name of "Amodimethicone" in "International Cosmetic Ingredient Dictionary and Handbook", Third Edition, published by The Cosmetic, Toiletry, and Fragrance Association (CTFA), U.S.A. This amino-modified silicone may preferably be used in the form of an aqueous emulsion, and its commercial products can include, for example, "SM 8704C" (trade name, product of Toray Silicone Co., Ltd.) and "DC 929" (trade name, product of Dow Corning Corp.).

(3) Further, polyether-modified silicones, methylphenylpolysiloxane, fatty-acid-modified silicones, alcohol-modified silicones, alkoxy-modified silicones, epoxy-modified silicones, fluorine-modified silicones, cyclic silicones, alkyl-modified silicones.

Among these, dimethylpolysiloxane is particularly preferred.

These silicones may be used either singly or in combination, and may amount to 0.2 to 5 wt. %, especially 0.5 to 2 wt. % of the whole composition.

The detergent composition according to the present invention may further contain a cationic polymer, and the resulting detergent composition can bring about superb conditioning effect. Examples of the cationic polymer can include cationized cellulose derivatives, cationic starch, cationic guar gum derivatives, homopolymer of diallyl quaternary ammonium salt, diallyl quaternary ammonium salt/acrylamide copolymer, quaternized polyvinylpyrrolidone derivatives, polyglycol polyamine condensation products, vinylimidazolium trichloride/vinylpyrrolidone copolymer, hydroxyethylcellulose/dimethyldiallylammonium chloride copolymer, vinylpyrrolidone/quaternized dimethylaminoethyl methacrylate copolymer, polyvinylpyrrolidone/alkyl amino-acrylate copolymer, polyvinylpyrrolidone/alkyl amino-acrylate/vinyl caprolactam copolymer, vinylpyrrolidone/methacrylamidopropyl chlorotrimethylammonium copolymer, alkyl acrylamide/acrylate/alkylaminoalkyl acrylamide/polyethylene glycol methacrylate copolymers, adipic acid/dimethylaminohydroxypropyl ethylenetriamine copolymer ("Cartaretin", trademark; product of Sandoz Chemicals Corp., U.S.A.), and cationic polymers disclosed in JP 53-139734 or JP60-36407. Of these, cationic cellulose derivatives are particularly preferred.

These cationic polymers may be used either singly or in combination, and may preferably amount to 0.01 to 5 wt. %, especially 0.05 to 1.5 wt. %, notably 0.1 to 0.8 wt. % of the whole composition. It is particularly preferred to use a silicone and a cationic polymer in combination in proportions of from 0.1 to 5 wt. %, respectively.

The detergent composition according to the present invention is in the form of an aqueous liquid making use of water as a medium, and may additionally contain one or more of ingredients used in general detergent compositions, for example, humectants such as propylene, glycerin, diethylene glycol monoethyl ether, sorbitol, and panthenol; colorants such as dyes and pigments; viscosity controlling agents such as methylcellulose, polyethylene glycol, and ethanol; pH regulators such as citric acid and potassium hydroxide; and salts such as sodium chloride, plant extracts, preservatives, disinfectants, chelating agents, vitamins, anti-inflammatories, anti-dandruff agents, fragrances, dyestuff, ultraviolet absorbers, antioxidants, and so on.

The detergent composition according to the present invention can be produced in a method known per se in the art, and can be formulated, for example, into body cleansing detergent preparations such as shampoos, body washes, face washes and hand washes.

EXAMPLE 1

Detergent compositions of the formulations shown in Table were produced, and their shelf stability levels were ranked. The results are also presented in Table 1.

Procedures

Each detergent composition was obtained by combining all the ingredients together, heating the resultant mixture to 80° C. and allowing the ingredients to melt, and then cooling the melt to 30° C. with stirring.

Ranking method

The individual detergent compositions were separately placed in 100-mL transparent glass containers, and shortly after their production and after stored at 20° C. or 40° C. for a month, their appearances were observed with the naked eye. The observation results were ranked in accordance with the following standards:

A: A pearly luster was even.

B: A pearly luster was uneven, and a separate, clear or emulsion-like layer was observed or a precipitate was observed on in a lower part.

C: No pearly luster was observed, and an appearance similar to that of a clear solution or an emulsion was observed.

TABLE 1

| | Invention product | | | | Comparative product |
|---|---|---|---|---|---|
| Ingredient (wt. %) | 1 | 2 | 3 | 4 | 1 |
| Sodium POE (3) lauryl ether sulfate | 20 | 20 | 15 | 15 | 20 |
| Lauryl amidopropyl-betaine | | | 5 | | |
| Coconut oil fatty acid monoethanol amide | | | | 3 | |
| POE (12) lauryl ether | | 2 | | | |
| Ethylene glycol distearate | 2 | 2 | 1 | 2 | 2 |
| n-Octyl glyceryl ether | 5 | 5 | 5 | 3 | |
| Purified water | Balance | Balance | Balance | Balance | Balance |
| Shortly after production | A | A | A | A | A |
| After stored at 20° C. for 1 month | A | A | A | A | B |
| After stored at 40° C. for 1 month | A | A | A | A | C |

EXAMPLE 2

A conditioning shampoo of the below-described formulation was produced in a manner known per se in the art.

The shampoo so obtained had an even pearly luster, and even after stored for a month, remained unchanged and stable.

| (Ingredient) | (wt. %) |
|---|---|
| Sodium POE (2) lauryl ether sulfate | 10 |
| Sodium lauryl sulfate | 5 |
| n-Octyl glyceryl ether | 3 |
| Ethylene glycol distearate | 2 |
| Silicone emulsion (Highly-polymerized dimethylpolysiloxane 25% contained; "BY-22-062", trade name, product of Dow Corning Toray Silicone Co., Ltd.) | 2 |
| Ethanol | 1 |
| Sodium benzoate | 0.3 |

-continued

| (Ingredient) | (wt. %) |
|---|---|
| Fragrance | 0.5 |
| Aqueous solution of citric acid | q.s. to pH 6.5 |
| Purified water | Balance |

EXAMPLE 3

A conditioning shampoo of the below-described formulation was produced in a manner known per se in the art.

The shampoo so obtained had an even pearly luster, and even after stored for a month, remained unchanged and stable.

| (Ingredient) | (wt. %) |
|---|---|
| Sodium POE (2) lauryl ether sulfate | 16 |
| Lauryl amidopropylbetaine | 3 |
| 2-Ethylhexyl glyceryl ether | 3 |
| Ethylene glycol distearate | 2.5 |
| Cetanol | 0.5 |
| Amino-modified silicone ("SM8704C", trade name; product of Toray Silicone Co., Ltd.) | 0.5 |
| Cationic cellulose ("JR400", trade name; product of Union Carbide Corp.) | 0.5 |
| Sodium benzoate | 0.3 |
| Fragrance | 0.5 |
| Aqueous solution of citric acid | q.s. to pH 6.5 |
| Purified water | Balance |

EXAMPLE 4

A conditioning shampoo of the below-described formulation was produced in a manner known per se in the art.

The shampoo so obtained had an even pearly luster, and even after stored for a month, remained unchanged and stable.

| (Ingredient) | (wt. %) |
|---|---|
| Sodium POE (2) lauryl ether sulfate | 18 |
| Coconut oil fatty acid monoethanolamide | 1 |
| POE (16) lauryl ether | 2 |
| n-Decyl glyceryl ether | 1.5 |
| Diethylene glycol monostearate | 2 |
| Chlorocetyl trimethyl ammonium | 0.5 |
| Silicone emulsion ("BY-22-062", trade name; product of Dow Corning Toray Silicone Co., Ltd.) | 3 |
| Cationic polymer ("Merquat 100", trade name; product of Calgon Corp.) | 0.5 |
| Ethanol | 2 |
| Disodium editate | 0.5 |
| Fragrance | 0.5 |
| Aqueous solution of citric acid | q.s. to pH 6.5 |
| Purified water | Balance |

What is claimed is:

1. An aqueous detergent composition comprising:

(A) 1 to 50 wt. % of a surfactant selected from the group consisting of an anionic surfactant, a nonionic surfactant and an amphoteric surfactant;

(B) 0.3 to 5 wt. % of a long-chain fatty acid glycol ester represented by formula (1):

(1)

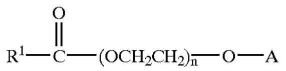

wherein $R^1$ is a linear or branched, alkyl or alkenyl group having 13 to 23 carbon atoms, n is an integer of 1 to 3, and A is a group

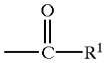

in which $R^1$ has the same meaning as defined above; and (C) 0.1 to 10 wt. % of a glyceryl ether having one or more linear or branched, alkyl or alkenyl groups having 4 to 12 carbon atoms.

2. The detergent composition according to claim 1, wherein said ingredient (A) comprises an anionic surfactant and a fatty acid amidopropyl betaine, a fatty acid alkanol amide or a polyoxyalkylene alkyl ether.

3. The detergent composition according to claim 1, wherein said surfactant comprises an anionic surfactant selected from the group consisting of alkyl sulfates, polyoxyalkylene alkyl ether sulfates and polyoxyalkylene alkenyl ether sulfates.

4. The detergent composition according to claim 1, wherein said surfactant comprises a nonionic surfactant selected from the group consisting of polyoxyalkylene alkyl ethers, polyoxyalkylene fatty acid esters, polyoxyalkylene sorbitan fatty acid esters, polyoxyalkylene sorbitol fatty acid esters, polyoxyalkylene glycerin fatty acid esters, monoglycerides, sorbitan fatty acids, fatty acid alkanolamides, and alkyl polyglycosides.

5. The detergent composition according to claim 1, wherein said surfactant comprises an amphoteric surfactant selected from the group consisting of fatty acid amidopropyl betaines, betaine acetates, betaine amidoacetates, sulfobetaines, amidosulfobetaines, phosphobetaines, alkylamine oxides, and amidoamine oxides.

6. The detergent composition according to claim 1, wherein surfactant comprises one or more of anionic surfactants, nonionic surfactants and amphoteric surfactants.

7. The detergent composition according to claim 1, wherein $R^1$ is a linear or branched alkyl or alkenyl group having 18 carbon atoms.

8. The detergent composition according to claim 1, wherein (B) is in an amount range of 0.8 to 3 wt. %.

9. The detergent composition according to claim 1, wherein (B) is ethylene glycol distearate.

10. The detergent composition according to claim 1, wherein said glyceryl ether has one or more linear or branched, alkyl or alkenyl groups having 6 to 11 carbon atoms.

11. The detergent composition according to claim 1, wherein (C) is present in an amount range of 1 to 5 wt. %.

12. The detergent composition according to claim 1, further comprising a silicone or combination of silicones.

13. The detergent composition according to claim 1, further comprising a cationic polymer or combination of cationic polymers.

14. The detergent composition according to claim 1, further comprising a silicone and a cationic polymer.

* * * * *

UNITED STATES PATENT AND TRADEMARK OFFICE

CERTIFICATE OF CORRECTION

PATENT NO. : 6,417,146 B1
DATED : July 9, 2002
INVENTOR(S) : Miyajima et al.

It is certified that error appears in the above-identified patent and that said Letters Patent is hereby corrected as shown below:

Title page, Item [54] and Column 1, lines 1-4,
The Title is incorrect. The Title should read as follows:

-- AN AQUEOUS DETERGENT COMPOSITION HAVING A SURFACTANT, A FATTY ACID GYLCOL ESTER AND A GLYCERYL ETHER --

Title page,
Item [30], the Foreign Application Priority Data is incorrect.
Item [30] should read as follows:

-- [30] Foreign Application Priority Data

Oct. 12, 1999 (JP)..............................11-289877 --

Signed and Sealed this

Tenth Day of December, 2002

JAMES E. ROGAN
*Director of the United States Patent and Trademark Office*